(12) United States Patent
Cramer et al.

(10) Patent No.: US 8,294,907 B2
(45) Date of Patent: Oct. 23, 2012

(54) INSPECTION METHOD AND APPARATUS, LITHOGRAPHIC APPARATUS, LITHOGRAPHIC PROCESSING CELL AND DEVICE MANUFACTURING METHOD

(75) Inventors: Hugo Augustinus Joseph Cramer, Eindhoven (NL); Antoine Gaston Marie Kiers, Veldhoven (NL)

(73) Assignee: ASML Netherlands B.V., Veldhoven (NL)

( * ) Notice: Subject to any disclaimer, the term of this patent is extended or adjusted under 35 U.S.C. 154(b) by 1091 days.

(21) Appl. No.: 11/580,265

(22) Filed: Oct. 13, 2006

(65) Prior Publication Data
US 2008/0088832 A1    Apr. 17, 2008

(51) Int. Cl.
*G01B 11/14*     (2006.01)
(52) U.S. Cl. .................................................. 356/625
(58) Field of Classification Search ............. 355/53, 355/77; 356/237.1–237.5, 399–401, 445, 356/625; 702/188
See application file for complete search history.

(56) References Cited

U.S. PATENT DOCUMENTS

| | | | |
|---|---|---|---|
| 5,703,692 A | 12/1997 | McNeil et al. | 356/445 |
| 5,719,796 A | 2/1998 | Chen | |
| 5,880,838 A | 3/1999 | Marx et al. | 356/351 |
| 5,963,329 A | 10/1999 | Conrad et al. | 356/372 |
| 6,429,930 B1* | 8/2002 | Littau et al. | 356/124 |
| 6,501,534 B1* | 12/2002 | Singh et al. | 355/55 |
| 6,608,690 B2 | 8/2003 | Niu et al. | 356/635 |
| 6,699,624 B2 | 3/2004 | Niu et al. | 430/5 |
| 6,704,661 B1 | 3/2004 | Opsal et al. | 702/27 |
| 6,721,691 B2 | 4/2004 | Bao et al. | 702/189 |
| 6,738,138 B2 | 5/2004 | Wei | 356/369 |
| 6,753,961 B1 | 6/2004 | Norton et al. | 356/364 |
| 6,762,111 B2 | 7/2004 | Fukuda | |
| 6,768,983 B1 | 7/2004 | Jakatdar et al. | 706/46 |
| 6,772,084 B2 | 8/2004 | Bischoff et al. | 702/127 |
| 6,785,638 B2 | 8/2004 | Niu et al. | 702/189 |
| 6,795,193 B2* | 9/2004 | Schulz | 356/445 |
| 6,813,034 B2 | 11/2004 | Rosencwaig et al. | 356/601 |
| 6,819,426 B2 | 11/2004 | Sezginer et al. | 356/401 |
| 6,856,408 B2 | 2/2005 | Raymond | 356/601 |
| 6,873,938 B1* | 3/2005 | Paxton et al. | 702/188 |
| 6,919,964 B2 | 7/2005 | Chu | 356/601 |
| 6,928,628 B2 | 8/2005 | Seligson et al. | 716/4 |
| 6,972,852 B2 | 12/2005 | Opsal et al. | 356/625 |
| 6,974,962 B2 | 12/2005 | Brill et al. | 250/548 |

(Continued)

FOREIGN PATENT DOCUMENTS
EP    1 628 164 A2    2/2006
(Continued)

OTHER PUBLICATIONS

English Language Abstract for JP 07-302826 A, published Nov. 14, 1995; 1 page.

(Continued)

*Primary Examiner* — Hung Henry Nguyen
*Assistant Examiner* — Steven H Whitesell Gordon
(74) *Attorney, Agent, or Firm* — Sterne, Kessler, Goldstein & Fox P.L.L.C.

(57) ABSTRACT

In a scatterometric method, different targets with different sensitivities to a parameter of interest are printed in a calibration matrix and different spectra obtained. Principal component analysis is applied to the different spectra to obtain a calibration function that is less sensitive to variation in the underlying structure than a calibration function obtained from spectra obtained from a single target.

12 Claims, 4 Drawing Sheets

U.S. PATENT DOCUMENTS

| | | | |
|---|---|---|---|
| 6,987,572 B2 | 1/2006 | Lakkapragada et al. | 356/601 |
| 7,046,376 B2 | 5/2006 | Sezginer | 356/601 |
| 7,061,615 B1 | 6/2006 | Lowe-Webb | 356/401 |
| 7,061,623 B2 | 6/2006 | Davidson | 356/497 |
| 7,061,627 B2 | 6/2006 | Opsal et al. | 356/601 |
| 7,068,363 B2 | 6/2006 | Bevis et al. | 356/237.5 |
| 7,069,182 B2 | 6/2006 | Johnson et al. | |
| 7,084,990 B2 | 8/2006 | Sasazawa et al. | |
| 7,151,594 B2 | 12/2006 | Den Boef et al. | |
| 7,198,873 B2 | 4/2007 | Geh et al. | |
| 7,515,253 B2 | 4/2009 | Bareket et al. | |
| 7,791,727 B2 | 9/2010 | Den Boef et al. | |
| 7,826,071 B2 | 11/2010 | Shchegrov et al. | |
| 2004/0070772 A1* | 4/2004 | Shchegrov et al. | 356/625 |
| 2004/0119970 A1 | 6/2004 | Dusa et al. | 356/237.1 |
| 2005/0106479 A1* | 5/2005 | Geh et al. | 430/30 |
| 2005/0128464 A1* | 6/2005 | Paxton et al. | 355/77 |
| 2005/0185174 A1* | 8/2005 | Laan et al. | 356/243.1 |
| 2006/0033921 A1 | 2/2006 | Den Boef et al. | 356/446 |
| 2006/0066855 A1 | 3/2006 | Den Boef et al. | 356/401 |
| 2006/0126074 A1 | 6/2006 | Van Der Werf et al. | 356/489 |
| 2006/0139592 A1 | 6/2006 | Den Boef et al. | 355/53 |

FOREIGN PATENT DOCUMENTS

| | | |
|---|---|---|
| EP | 1 628 164 A3 | 4/2006 |
| JP | 07-302826 A | 11/1995 |
| JP | 2000-517473 A | 12/2000 |
| JP | 2002-260994 A | 3/2002 |
| JP | 2003-224057 A | 8/2003 |
| JP | 2003-344029 A | 12/2003 |
| JP | 2004-507719 A | 3/2004 |
| JP | 2004-200680 A | 7/2004 |
| JP | 2004-235460 A | 8/2004 |
| JP | 2004-529330 A | 9/2004 |
| JP | 2004-536314 A | 12/2004 |
| JP | 2005-094015 A | 4/2005 |
| JP | 2005-106754 A | 4/2005 |
| JP | 2005-127830 A | 5/2005 |
| JP | 2005-150760 A | 6/2005 |
| JP | 2006-060214 A | 3/2006 |
| JP | 2006-512561 A | 4/2006 |
| JP | 2008-530519 A | 8/2008 |

OTHER PUBLICATIONS

English Language Description and Claims for JP 2000-517473 A, published Dec. 26, 2000; 8 pages.

English Language Abstract for JP 2002-260994 A, published Sep. 13, 2002; 1 page.

English Language Abstract for JP 2003-224057 A, published Aug. 8, 2003; 1 page.

English Language Abstract for JP 2003-344029 A, published Dec. 3, 2003; 2 pages.

English Language Abstract for JP 2004-200680 A, published Jul. 15, 2004; 2 pages.

English Language Abstract for JP 2004-235460 A, published Aug. 19, 2004; 1 page.

English Language Description and Claims for JP 2004-507719 A, published Mar. 11, 2004; 12 pages.

English Language Description and Claims for JP 2004-529330 A, published Sep. 24, 2004; 7 pages.

English Language Description and Claims for JP 2004-536314 A, published Dec. 2, 2004; 8 pages.

English Language Abstract for JP 2005-094015 A, published Apr. 7, 2005; 2 pages.

English Language Abstract for JP 2005-106754 A, published Apr. 21, 2005; 1 page.

English Language Abstract for JP 2005-127830 A, published May 19, 2005; 1 page.

English Language Abstract for JP 2005-150760 A, published Jun. 9, 2005; 2 pages.

English Language Abstract for JP 2006-060214 A, published Mar. 2, 2006; 2 pages.

English Language Description and Claims for JP 2006-512561 A, published Apr. 13, 2006; 11 pages.

English Language Description and Claims for JP 2008-530519 A, published Aug. 7, 2008; 7 pages.

English Translation of Notice of Reasons for Rejection directed to related Japanese Patent Application No. 2007-261443, mailed on Nov. 1, 2010 from the Japanese Patent Office; 3 pages.

* cited by examiner

INSPECTION METHOD AND APPARATUS, LITHOGRAPHIC APPARATUS, LITHOGRAPHIC PROCESSING CELL AND DEVICE MANUFACTURING METHOD

FIELD

The invention relates to a method of inspection usable, for example, in the manufacture of devices by a lithographic technique and to a method of manufacturing devices using a lithographic technique.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. comprising part of, one, or several dies) on a substrate (e.g. a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the scanning"-direction) while synchronously scanning the substrate parallel or anti parallel to this direction. It is also possible to transfer the pattern from the patterning device to the substrate by imprinting the pattern onto the substrate.

In order to monitor the lithographic process, one or more parameters of the patterned substrate, for example the overlay error between successive layers formed in or on it, are typically measured. There are various techniques for making measurements of the microscopic structures formed in a lithographic process, including the use of a scanning electron microscope and various specialized tools. One form of specialized inspection tool is a scatterometer in which a beam of radiation is directed onto a target on the surface of the substrate and one or more properties of the scattered or reflected beam are measured. By comparing one or more properties of the beam before and after it has been reflected or scattered by the substrate, one or more properties of the substrate may be determined. This may be done, for example, by comparing the reflected beam with data stored in a library of known measurements associated with a known substrate property. Two main types of scatterometer are known. A spectroscopic scatterometer directs a broadband radiation beam onto the substrate and measures the spectrum (intensity as a function of wavelength) of the radiation scattered into a particular narrow angular range. An angularly resolved scatterometer uses a monochromatic radiation beam and measures the intensity of the scattered radiation as a function of angle. An ellipsometer also measures polarization state.

There are two basic methods to determine the value of a parameter of interest of the target, e.g. critical dimension (CD), from the data (referred to as a spectrum) obtained in the scatterometer: iterative modeling and library searching. In the iterative modeling technique, a theoretical model of the target structure is used to calculate the spectrum that would be obtained from the target as a function of the parameter of interest. Starting with an initial or seed value, a predicted spectrum is calculated and compared to the measured spectrum so that the estimation of the parameter value can be improved. This process is repeated for a number of iterations until the predicted spectrum matches the measured spectrum to within a desired margin of error at which point it is assumed that the actual value of the parameter is equal to the predicted value of the parameter used to obtain the predicted spectrum to within a desired degree of precision.

In a library search, a library of predicted spectra is constructed, again using a model relating spectra to parameter values, and the measured spectra is compared to the library entries to determine the closest match. Interpolation between entries can be used to increase accuracy. The number of entries in the library is determined by the range of possible parameter values expected, which is dependent on how accurately the parameter value can be guessed in advance, and the desired accuracy of measurement.

In almost all cases, several parameters of the target may vary and affect the measured spectrum. The time taken to construct and search a library and to perform an iteration tends to increase exponentially with an increase in the number of parameters. Further, the number of iterations required to achieve a desired level of accuracy may increase dramatically with error in the initial guess.

Furthermore, the accuracy is limited by the combination of the signal to noise ratio of the scatterometer and the condition number of the Jacobian matrix, the latter representing the derivative of the scatterometry signal with respect to each of the measurement parameters. This condition number gets worse, and hence the accuracy gets worse, with increasing number of measurement parameters. As an example, the accuracy of CD measurement may improve by a factor of between 3 and 100 when changing from a 3-parameter model of the target structure to a 1-parameter model by setting the other parameters to a fixed value.

SUMMARY

It is desirable, for example, to provide an improved method of guessing an initial or seed value of one or more parameters of a target structure to be used in a method of determining the actual value(s) of the parameter for a given measured target.

According to an aspect of the invention, there is provided a method of measuring one or more parameters of a plurality of target patterns which have been printed in one or more fields on one or more substrates by a lithographic process, the method comprising:

directing an inspection beam of radiation onto a first one of the plurality of target patterns and measuring the radiation reflected or scattered therefrom to obtain first measurement data;

processing the first measurement data to obtain a first value related to a parameter of the first one of the plurality of target patterns;

directing an inspection beam of radiation onto a second one of the plurality of target patterns and measuring the radiation reflected or scattered therefrom to obtain second measurement data; and processing the second measurement data to obtain a second value related to a parameter of the second one of the plurality of target patterns, wherein in the processing the second measurement data a seed value derived from the first value is used to assist in obtaining the second value.

According to an aspect of the invention, there is provided a device manufacturing method, comprising:

printing a plurality of target patterns and a device pattern in one or more fields on each of a first substrate and a second substrate by a lithographic process;

directing an inspection beam of radiation onto a first one of the plurality of target patterns and measuring the radiation reflected or scattered therefrom to obtain first measurement data;

processing the first measurement data to obtain a first value related to a parameter of the first one of the plurality of target patterns;

directing an inspection beam of radiation onto a second one of the plurality of target patterns and measuring the radiation reflected or scattered therefrom to obtain second measurement data; and processing the second measurement data to obtain a second value related to a parameter of the second one of the plurality of target patterns, wherein in the processing the second measurement data, a seed value derived from the first value is used to assist in obtaining the second value.

According to an aspect of the invention, there is provided an inspection apparatus configured to determine a value related to a parameter of a target pattern printed on a substrate by a lithographic process used to manufacture a device layer on a substrate, the apparatus comprising:

an illumination optical system arranged to direct an inspection beam of radiation on to the target pattern;

a projection optical system arranged to project radiation reflected or scattered by the target pattern onto a detector to obtain a scatterometric spectra;

a calculator arranged to calculate the value using the scatterometric spectra and a seed value; and a storage device arranged to store values calculated by the calculator and to provide one or more stored values to the calculator as a seed value.

According to an aspect of the invention, there is provided a method of measuring one or more parameters of a plurality of target patterns which have been printed in one or more fields on one or more substrates by a lithographic process, the method comprising:

directing an inspection beam of radiation onto a first one of the plurality of target patterns and measuring the radiation reflected or scattered therefrom to obtain first measurement data;

directing an inspection beam of radiation onto a second one of the plurality of target patterns and measuring the radiation reflected or scattered therefrom to obtain second measurement data; and processing the first and second measurement data to obtain first and second values respectively related to a parameter of the first and second ones of the plurality of target patterns using a model relating to and linking the parameter of both the first and second ones of the plurality of target patterns.

According to an aspect of the invention, there is provided an inspection apparatus configured to determine a plurality of values related to a parameter of a plurality of target patterns printed on a substrate by a lithographic process used to manufacture a device layer on a substrate, the apparatus comprising:

an illumination optical system arranged to direct an inspection beam of radiation on to each of the plurality of target patterns;

a projection optical system arranged to project radiation reflected or scattered by each of the plurality of target patterns onto a detector to obtain scatterometric spectra;

a calculator arranged to calculate the value using the scatterometric spectra and a model; and a storage device arranged to store the model, wherein the model relates to and links the parameter of each of the plurality of target patterns.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

Figure 1A:
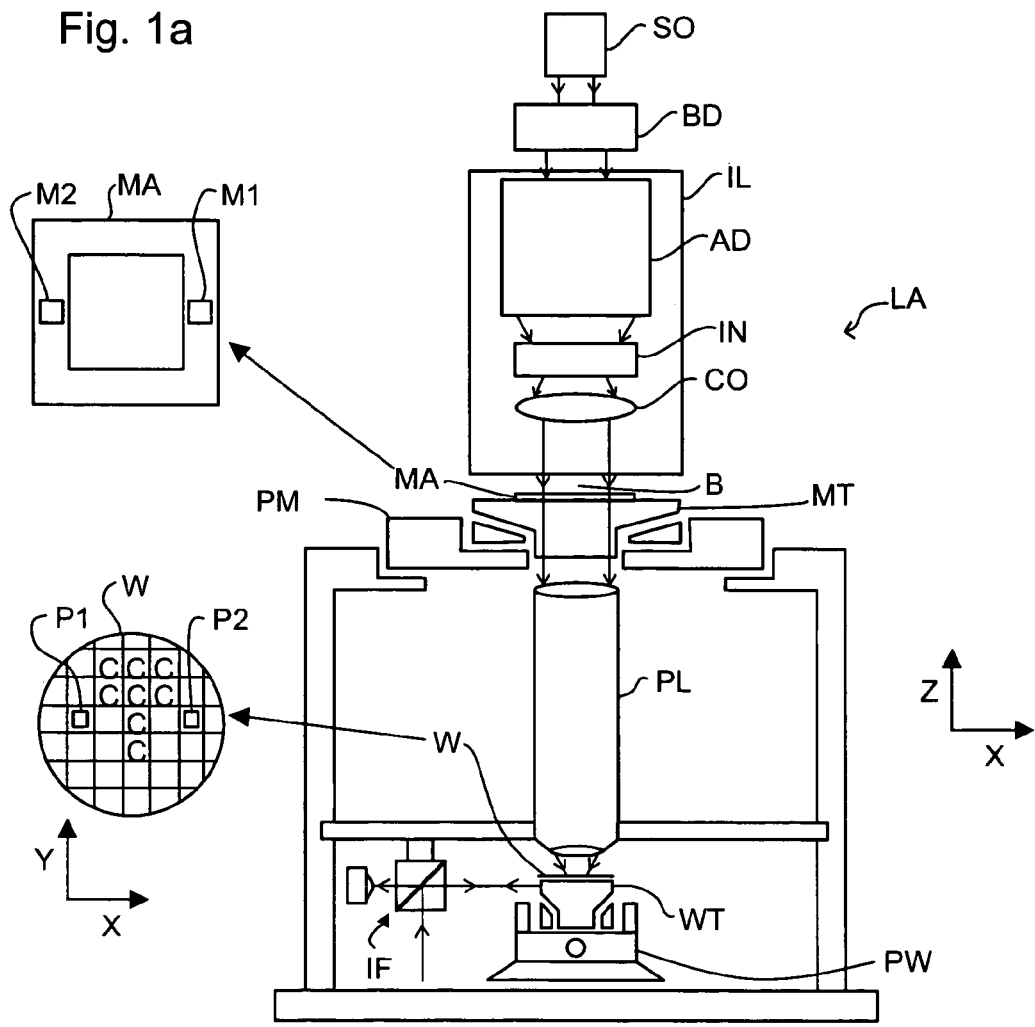
FIG. 1a depicts a lithographic apparatus.

FIG. 1a schematically depicts a lithographic apparatus. The apparatus comprises:

an illumination system (illuminator) IL configured to condition a radiation beam B (e.g. UV radiation or EUV radiation);

a support structure (e.g. a mask table) MT constructed to support a patterning device (e.g. a mask) MA and connected to a first positioner PM configured to accurately position the patterning device in accordance with certain parameters;

a substrate table (e.g. a wafer table) WT constructed to hold a substrate (e.g. a resist coated wafer) W and connected to a second positioner PW configured to accurately position the substrate in accordance with certain parameters; and a projection system (e.g. a refractive projection lens system) PL configured to project a pattern imparted to the radiation beam B by patterning device MA onto a target portion C (e.g. comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate.

It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more substrate tables (and/or two or more support structures). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1a, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross section.

The radiation beam B is incident on the patterning device (e.g., mask) MA, which is held on the support structure (e.g., mask table) MT, and is patterned by the patterning device. Having traversed the patterning device MA, the radiation beam B passes through the projection system PL, which focuses the beam onto a target portion C of the substrate W. With the aid of the second positioner PW and position sensor IF (e.g. an interferometric device, linear encoder or capacitive sensor), the substrate table WT can be moved accurately, e.g. so as to position different target portions C in the path of the radiation beam B. Similarly, the first positioner PM and another position sensor (which is not explicitly depicted in FIG. 1a) can be used to accurately position the patterning device MA with respect to the path of the radiation beam B, e.g. after mechanical retrieval from a mask library, or during a scan. In general, movement of the support structure MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the support structure MT may be connected to a short-stroke actuator only, or may be fixed. Patterning device MA and substrate W may be aligned using patterning device alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device MA, the patterning device alignment marks may be located between the dies.

The depicted apparatus could be used in at least one of the following modes:

1. In step mode, the support structure MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the support structure MT and the substrate table WT are scanned synchronously while a pattern imparted to the radiation beam is projected onto a target portion C (i.e. a single dynamic exposure). The velocity and direction of the substrate table WT relative to the support structure MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning-motion determines the height (in the scanning direction) of the target portion.

3. In another mode, the support structure MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 1B:
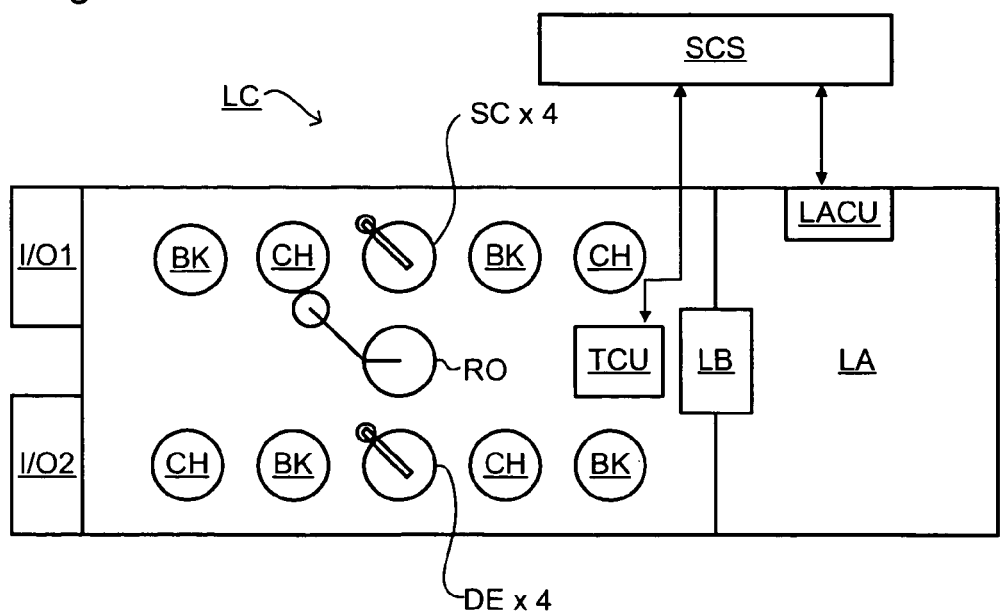
FIG. 1b depicts a lithographic cell or cluster.

As shown in FIG. 1b, the lithographic apparatus LA forms part of a lithographic cell LC, also sometimes referred to as a lithocell or lithocluster, which also includes apparatus to perform one or more pre- and post-exposure processes on a substrate. Conventionally these include one or more spin coaters SC to deposit a resist layer, one or more developers DE to develop exposed resist, one or more chill plates CH and one or more bake plates BK. A substrate handler, or robot, RO picks up a substrate from input/output ports I/O1, I/O2, moves it between the different process devices and delivers it to the loading bay LB of the lithographic apparatus. These devices, which are often collectively referred to as the track, are under the control of a track control unit TCU which is itself controlled by the supervisory control system SCS, which also controls the lithographic apparatus via lithographic control unit LACU. Thus, the different apparatus may be operated to maximize throughput and processing efficiency.

In order that the substrate that is exposed by the lithographic apparatus is exposed correctly and consistently, it is desirable to inspect an exposed substrate to measure one or more properties such as overlay error between subsequent layers, line thickness, critical dimension (CD), etc. If an error is detected, an adjustment may be made to an exposure of one or more subsequent substrates, especially if the inspection can be done soon and fast enough that another substrate of the same batch is still to be exposed. Also, an already exposed substrate may be stripped and reworked—to improve yield—or discarded—thereby avoiding performing an exposure on a substrate that is known to be faulty. In a case where only some target portions of a substrate are faulty, a further exposure may be performed only on those target portions which are good. Another possibility is to adapt a setting of a subsequent process step to compensate for the error, e.g. the time of a trim etch step can be adjusted to compensate for substrate-to-substrate CD variation resulting from the lithographic process step.

An inspection apparatus is used to determine one or more properties of a substrate, and in particular, how one or more properties of different substrates or different layers of the same substrate vary from layer to layer and across a substrate. The inspection apparatus may be integrated into the lithographic apparatus LA or the lithocell LC or may be a stand-alone device. To enable most rapid measurements, it is desirable that the inspection apparatus measure one or more properties in the exposed resist layer immediately after the exposure. However, the latent image in the resist has a very low contrast—there is only a very small difference in refractive index between the part of the resist which has been exposed to radiation and that which has not—and not all inspection apparatus have sufficient sensitivity to make useful measurements of the latent image. Therefore measurements may be taken after the post-exposure bake step (PEB) which is customarily the first step carried out on an exposed substrate and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibility for rework of a faulty substrate but may still provide useful information, e.g. for the purpose of process control.

Figure 2:
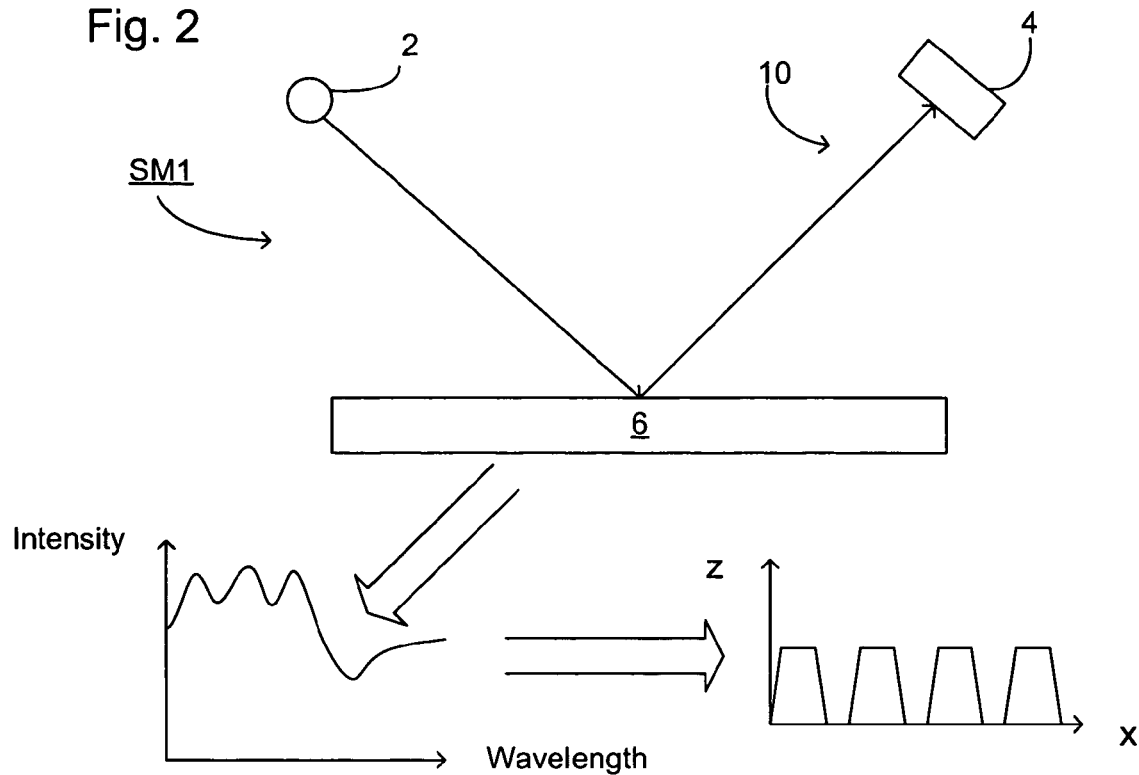
FIG. 2 depicts a first scatterometer according to an embodiment of the invention.

FIG. 2 depicts a scatterometer which may be used in an embodiment of the invention. It comprises a broadband (white light) radiation projector 2 which projects radiation onto a substrate W. The reflected radiation is passed to a spectrometer detector 4, which measures a spectrum 10 (i.e. a measurement of intensity as a function of wavelength) of the specular reflected radiation. From this data, the structure or profile giving rise to the detected spectrum may be reconstructed, e.g. by Rigorous Coupled Wave Analysis and non-linear regression or by comparison with a library of simulated spectra as shown at the bottom of FIG. 2. In general, for the reconstruction, the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Figure 3:
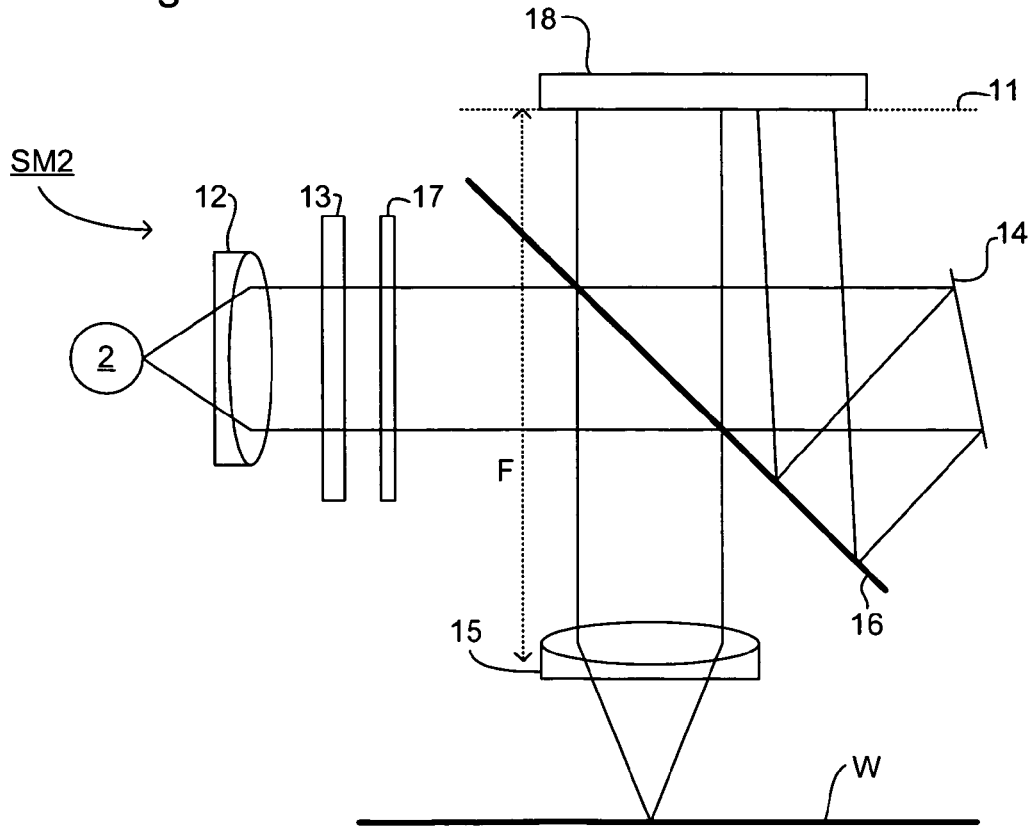
FIG. 3 depicts a second scatterometer according to an embodiment of the invention.

Another scatterometer that may be used with an embodiment of the invention is shown in FIG. 3. In this device, the radiation emitted by radiation source 2 is focused using lens system 12 through interference filter 13 and polarizer 17, reflected by partially reflective surface 16 and is focused onto substrate W via a microscope objective lens 15, which has a high numerical aperture (NA), desirably at least 0.9 or at least 0.95. An immersion scatterometer may even have a lens with a numerical aperture over 1. The reflected radiation then transmits through partially reflective surface 16 into a detector 18 in order to have the scatter spectrum detected. The detector may be located in the back-projected pupil plane 11, which is at the focal length of the lens 15, however the pupil plane may instead be re-imaged with auxiliary optics (not shown) onto the detector 18. The pupil plane is the plane in which the radial position of radiation defines the angle of incidence and the angular position defines the azimuth angle of the radiation. The detector is desirably a two-dimensional detector so that a two-dimensional angular scatter spectrum (i.e. a measurement of intensity as a function of angle of scatter) of the substrate target can be measured. The detector 18 may be, for example, an array of CCD or CMOS sensors, and may have an integration time of, for example, 40 milliseconds per frame.

A reference beam is often used, for example, to measure the intensity of the incident radiation. To do this, when the radiation beam is incident on the partially reflective surface 16 part of it is transmitted through the surface as a reference beam towards a reference mirror 14. The reference beam is then projected onto a different part of the same detector 18.

One or more interference filters 13 is available to select a wavelength of interest in the range of, say, 405-790 nm or even lower, such as 200-300 nm. The interference filter(s) may be tunable rather than comprising a set of different filters. A grating could be used instead of or in addition to one or more interference filters.

The detector 18 may measure the intensity of scattered radiation at a single wavelength (or a narrow wavelength range), the intensity separately at multiple wavelengths or the intensity integrated over a wavelength range. Further, the detector may separately measure the intensity of transverse magnetic- and transverse electric-polarized radiation and/or the phase difference between the transverse magnetic- and transverse electric-polarized radiation.

Using a broadband radiation source (i.e. one with a wide range of radiation frequencies or wavelengths—and therefore of colors) is possible, which gives a large etendue, allowing the mixing of multiple wavelengths. The plurality of wavelengths in the broadband desirably each has a bandwidth of $\delta\lambda$ and a spacing of at least $2\delta\lambda$ (i.e. twice the wavelength bandwidth). Several "sources" of radiation may be different portions of an extended radiation source which have been split using, e.g., fiber bundles. In this way, angle resolved scatter spectra may be measured at multiple wavelengths in parallel. A 3-D spectrum (wavelength and two different angles) may be measured, which contains more information than a 2-D spectrum. This allows more information to be measured which increases metrology process robustness. This is described in more detail in European patent application publication EP1,628,164A, which document is hereby incorporated in its entirety by reference.

The target on substrate W may be a grating which is printed such that after development, the bars are formed of solid resist lines. The bars may alternatively be etched into the substrate. The target pattern is chosen to be sensitive to a parameter of interest, such as focus, dose, overlay, chromatic aberration in the lithographic projection apparatus, etc., such that variation in the relevant parameter will manifest as variation in the printed target.

Figure 4:
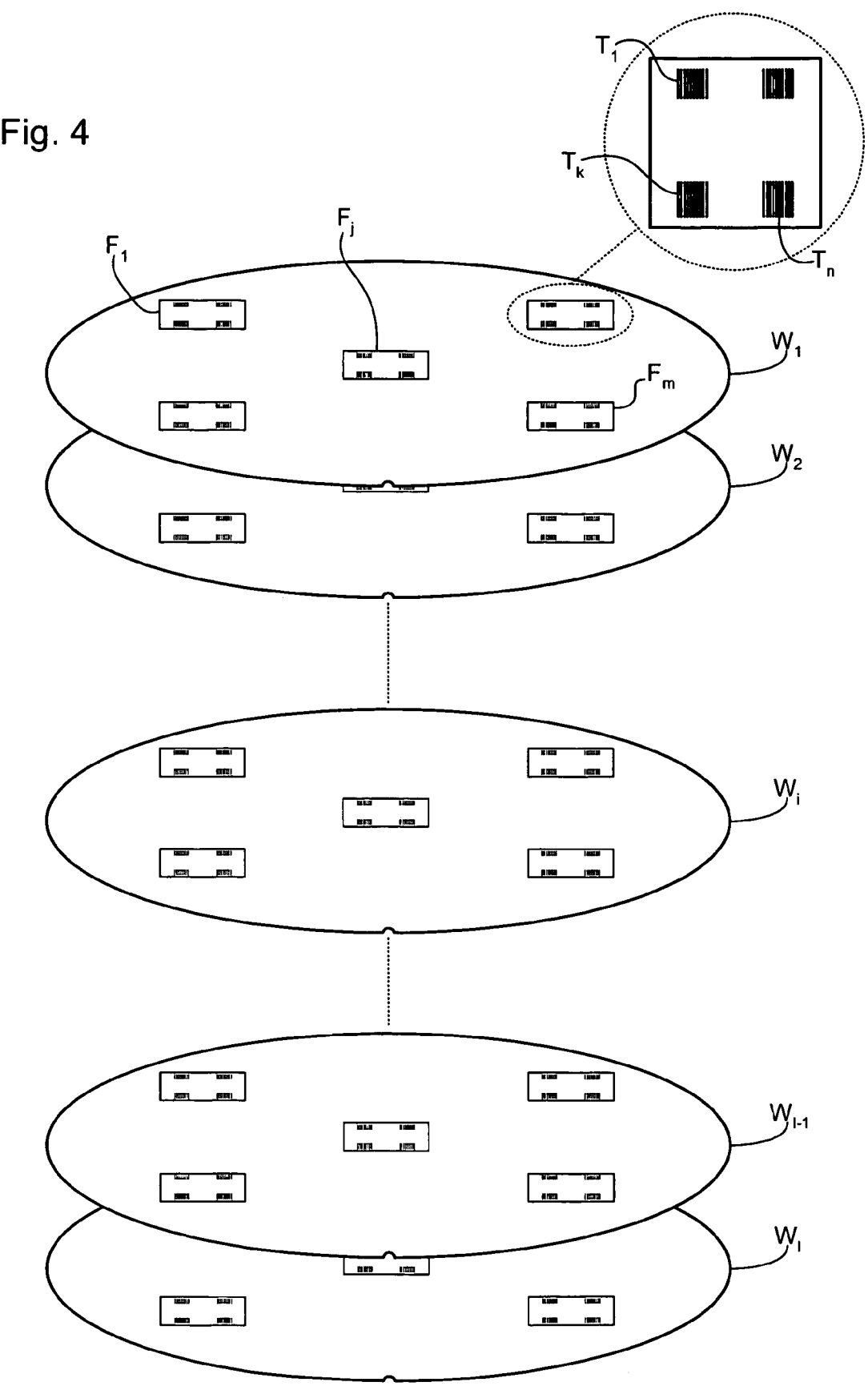
FIG. 4 depicts targets printed in fields on substrates in a method according to an embodiment of the invention.

As shown in FIG. 4, in a conventional lithographic process, a pattern, which may include a plurality of measurement targets $T_1$ to $T_n$, is printed on each of a plurality of fields $F_1$ to $F_m$ on each of a plurality of substrates $W_1$ to $W_l$ forming a batch. Although identical process parameters are used for each exposure and process step, variations do inevitably occur between the images printed, some random and some systematic. Some systematic errors, e.g. due to patterning device or projection system errors, repeat from field to field while others, e.g. due to substrate table or process errors, repeat from substrate to substrate. Some variations may be random from substrate to substrate, but affect the substrate as a whole or exhibit only gradual variation over the substrate. As an example, CD variation due to temperature variation and differences of the post-exposure bake plate exhibit a slowly varying across-substrate fingerprint. Using the systematic properties of the variation it is possible to predict the value of a parameter of interest over a large number of combinations of one or more locations on one or more substrates from a limited number of measurements. An embodiment of the invention aims to exploit this predictability to improve the initial guess to be used in determining the value of a parameter of interest from scatterometry data. The approach of an embodiment of the invention applies to both iterative and library search methods and to combinations thereof.

Figure 5:
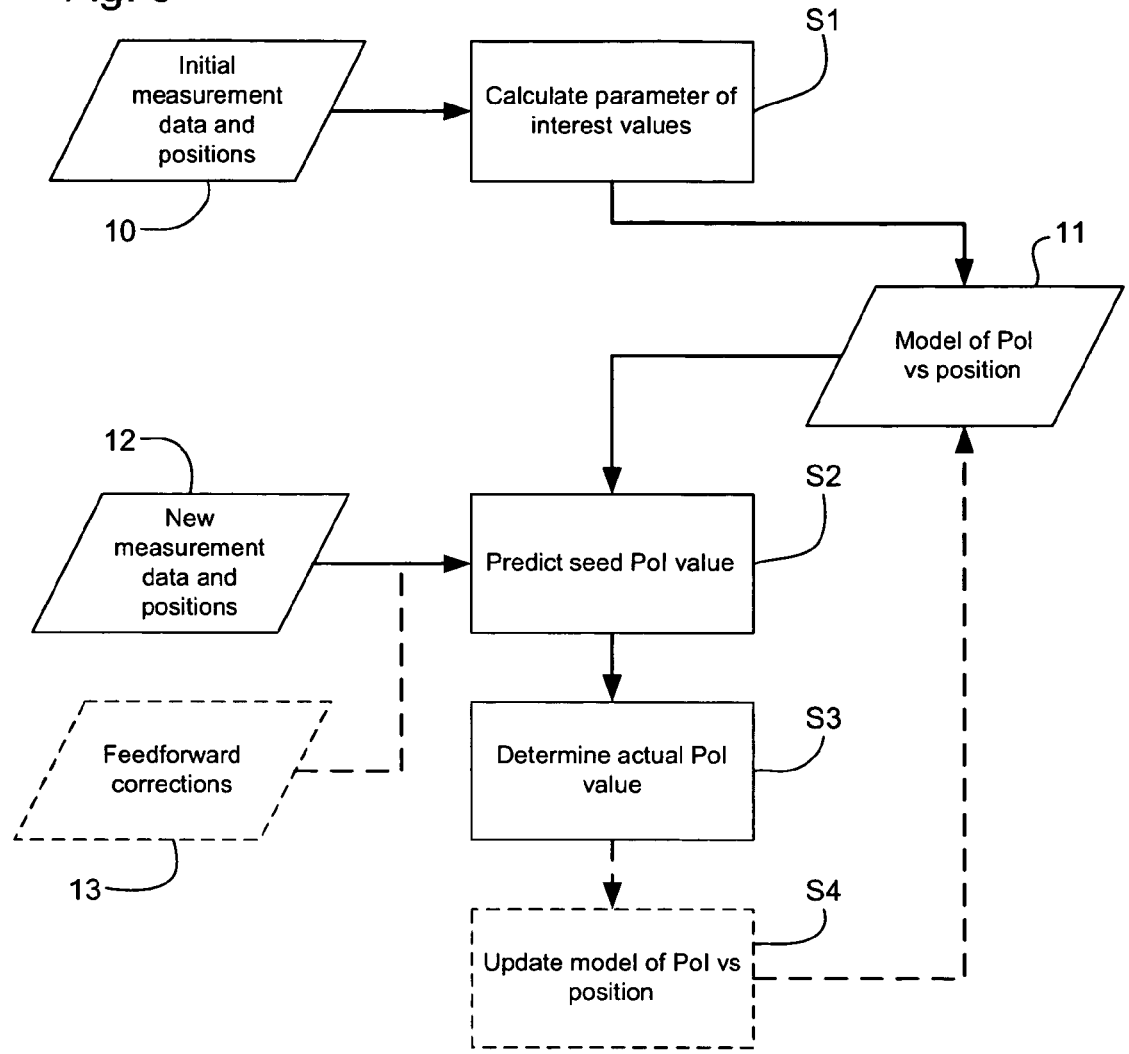
FIG. 5 is a flow chart of a method according to an embodiment of the invention.

Thus, in an embodiment of the invention, shown in FIG. 5, scatterometry measurements 10 are taken from an initial set of targets and processed S1 in a known manner to obtain values for one or more target parameters of interest, e.g. thickness of the bottom anti-reflective coating (BARC). The initial set of targets may be on a first substrate of a batch or a "send-ahead" substrate, that is a substrate that is exposed ahead of a batch, but with the same relevant process parameters, and measured to verify in advance the process to be carried out on the full batch. The initial set of targets should comprise a sufficient number of targets, for example from 5 to 100 with a sufficient spread across a field and/or the substrate to be representative of variation in the parameter of interest across the field and/or the substrate. Conventional analysis techniques, such as a library search or iterative approach as described above, may be used to derive a value or values for the parameter of interest for each target. Known statistical techniques, such as fitting a combined intra-field and inter-field polynomial model, may then be used to generate a model 11 of the parameter of interest (PoI) as a function of position in the field and or the substrate.

One or more subsequent substrates in the batch are exposed according to the same process and measured to provide scatterometry data 12. Based on the position of the target being measured, the model 11 is used to generate one or more seed values as a prediction of the likely actual value(s) of the parameter of interest. This is used in an analysis, again using conventional techniques such as a library search or iterative process, to derive values for the parameter of interest. In this way, the systematic variations in the parameter of interest are predicted and the seed value is close to the actual value, differing only by the random error component. Because the seed value is, in most cases, close to the actual value, a library search may be performed more quickly and a smaller library used and an iterative approach will close in on the actual value in fewer iterations. Alternatively, the predicted value may be accurate enough to be used as a fixed parameter, thus having the advantage mentioned above, as well as improving the accuracy of any other parameter(s) of interest.

The method may be an iterative process also or alternatively, in that the method is first carried out for one field of the first substrate to provide a model of the parameter of interest as a function of position within the field. This model is then used to provide one or more seed values for analysis of the measurement data from other fields of the first substrate which then enables construction of a model of the parameter of interest as a function of position on the substrate. The number of iterations to achieve an answer of the desired accuracy is reduced at each step. Thus, in an example, 5 iterations may be used to obtain a value for the targets of the first field of the first substrate, 3 iterations for the targets of subsequent fields of the first substrate and only 1 for the targets of one or more subsequent substrates. For this reason, an embodiment of the invention has an advantage in in-line monitoring applications, where measurements are to be taken of all or most fields of all substrates in a batch. Since 5 iterations of an analysis of a scatterometry spectrum may take 1 or 2 seconds, without an embodiment of the invention, such monitoring may cause a significant loss of throughput. Furthermore, as actual parameter values are calculated for one or more subsequent substrates, the model may be updated.

Another optional refinement is that data relating to a known characteristic of the lithographic apparatus, track or cell, for example the "first wafer effect", may be collated as a feed forward correction 13 and combined with the seed value generated by the model 11 to derive the actual seed value used in the analysis S3 of the actual value of the parameter of interest for a given measurement target. Feed forward correction data 13 may also take into account deliberately introduced process variation to correct errors noted by this or other monitoring processes. For example, measurement of CD by scatterometry may reveal values in an early substrate of a batch deviating from the desired values so that a dose change is made to compensate when exposing a later batch or substrate.

When applied to a library search approach to obtaining parameter values from the scatterometric data, an embodiment of the invention reduces the size of the library that needs to be constructed and/or searched. It is only needed to search and/or construct a library space that spans parameter values within the random error range of the seed value. If the accuracy of the seed value is sufficient it may be used as a fixed value, thus improving the accuracy of the values of one or more other parameters of interest.

In a simple embodiment of the invention, all measurement targets are at the same positions within each field and the layout of fields on each substrate is the same. Thus the seed value $P_s(i,j,k)$ for target k in field j of substrate i (i>1) can be given as follows:

$$P_s(i,j,k)=P_a(1,j,k)+\Delta(i,j,k) \quad (1)$$

where $P_a$ is the actual value of the parameter for the target k in field j of substrate 1, the initial or send-ahead substrate, and $\Delta(i,j,k)$ is the feed-forward correction.

A simple extension of the above embodiment is to average previous results, so that:

$$P_s(i, j, k) = \frac{\sum_{n=1}^{i} P_a(n, j, k)}{i} + \Delta(i, j, k) \quad (2)$$

In many cases however such a simple scheme cannot be implemented for all targets—damage to a desired target may make it unusable. In that case, another target may be used, for which no previous actual data is available, and the seed value is interpolated or extrapolated from data relating to one or more neighboring targets, taking into account its position relative to that target(s).

In a lithographic apparatus with multiple substrate tables and lithographic cells with multiple process units for carrying out a given step, such as multiple resist coaters, systematic errors may be different between the different tables or process units. In this case, after the initial substrate, the seed data may be derived only from an earlier substrate that has traveled the same path, i.e. been exposed on the same table and processed by the same process unit(s), as the given substrate under consideration. This may be effected by treating the one or more substrates within a batch that travel each possible path as one or more separate sub-batches.

In cases where multiple batches of the same process are made, data from an earlier batch may be used to generate seed data for the analysis of targets in one or more subsequent batches.

Figure 6:
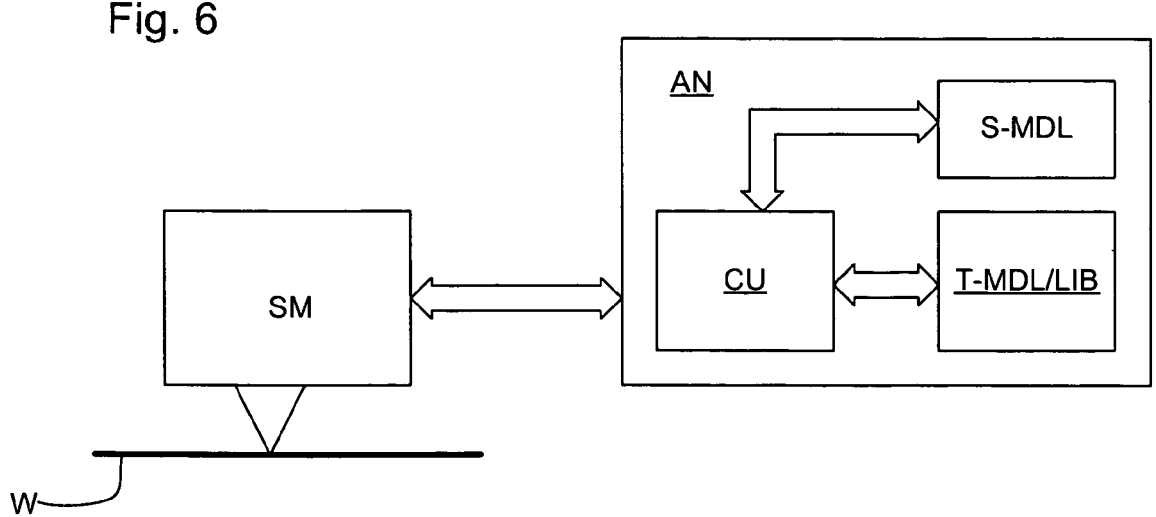
FIG. 6 depicts an inspection tool according to an embodiment of the invention.

The method may be effected by a scatterometry device as shown in FIG. 6. This device comprises a scatterometer SM, which may be of any of the types described above and generates the scatterometry data from one or more targets on a substrate, and an analysis unit AN configured to derive values of the parameter of interest from the scatterometry data. The analysis unit AN comprises a calculating unit CU configured to perform the various calculations necessary, a target model or library storage device T-MDL/LIB which stores a model of the scatterometry data as a function of the parameter of interest or pre-calculated spectra for different parameter values, and a seed model storage device S-MDL which stores a model used to predict the seed values. The analysis unit may be a specifically constructed device or may be embodied as a software operating on a general purpose computer.

In a more advanced embodiment of the invention, the stepwise approach described above may be replaced by a one-step approach. In such an approach, the raw measurement data of the first measurements are combined with the raw measurement data of the second measurements. In order to derive the values of the parameter of interest, a model is used that covers both the parameter of the features of the first measurements as well as the parameter of the features of the second measurements where the parameter of interest of the first measurements are linked to the parameter of interest of the second measurements. In particular in an iterative approach such a method may lead to significant improvement in iteration steps as well as improvement of the accuracy of the parameter of interest.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

The invention claimed is:

1. A method of measuring one or more parameters of a plurality of target patterns which have been printed in one or more fields on a substrate by a lithographic process, the method comprising:

directing an inspection beam of radiation onto a first one of the plurality of target patterns on the substrate and measuring radiation reflected or scattered therefrom to obtain first measurement data;

processing the first measurement data to obtain a first value related to a parameter of the first one of the plurality of target patterns;

directing the inspection beam of radiation onto a second one of the plurality of target patterns on the substrate and measuring radiation reflected or scattered therefrom to obtain second measurement data;

processing the second measurement data to obtain a second value related to a parameter of the second one of the plurality of target patterns on the substrate, wherein in the processing the second measurement data a seed value derived from the first value is used to assist in obtaining the second value, and wherein the processing the first measurement data and the processing the second measurement data comprise a search of a library space, the library space constructed based on a random error range of the seed value.

2. The method of claim 1, wherein the first and second ones of the plurality of targets are located on the substrate, but in different fields.

3. The method of claim 2, wherein the first and second ones of the plurality of targets are located in a same relative position within their respective fields.

4. The method of claim 1, wherein the directing the inspection beam of radiation onto the first one of the plurality of target patterns and the processing the first measurement data are repeated a plurality of times for a first plurality of the target patterns located at respective different positions to obtain a first set of values for the parameter of the respective ones of the first plurality of target patterns and the seed value is derived from the first set of values.

5. The method of claim 4, wherein the second one of the target patterns is located at a position that does not correspond to the position within the field or substrate of any of the first plurality of target patterns and the seed value is derived by interpolation, extrapolation or modeling.

6. The method of claim 1, further comprising:
directing the inspection beam of radiation onto a third one of the plurality of target patterns and measuring radiation reflected or scattered therefrom to obtain third measurement data; and
processing the third measurement data to obtain a third value related to the parameter of the third one of the plurality of target patterns,
wherein in the processing the third measurement data, a second seed value derived from the first value, the second value, or both, is used.

7. The method of claim 1, wherein the processing the first measurement data and the processing the second measurement data further comprise interpolation or fitting methods.

8. The method of claim 1, wherein the processing the first measurement data and the processing the second measurement data comprise iterative calculations.

9. The method of claim 1, further comprising adjusting the seed value to effect a feed forward correction.

10. The method of claim 1, further comprising:
determining, prior to the processing the second measurement data, the random error range of the seed value, wherein the random error range is limited.

11. A device manufacturing method, comprising:
printing a plurality of target patterns and a device pattern in one or more fields on by a lithographic process;
directing an inspection beam of radiation onto a first one of the plurality of target patterns on the substrate and measuring radiation reflected or scattered therefrom to obtain first measurement data;
processing the first measurement data to obtain a first value related to a parameter of the first one of the plurality of target patterns;
directing the inspection beam of radiation onto a second one of the plurality of target patterns on the substrate and measuring radiation reflected or scattered therefrom to obtain second measurement data;
processing the second measurement data to obtain a second value related to a parameter of the second one of the plurality of target patterns,
wherein in the processing the second measurement data, a seed value derived from the first value is used to assist in obtaining the second value, and
wherein the processing the first measurement data and the processing the second measurement data comprise a search of a library space, the library space constructed based on a random error range of the seed value.

12. The device manufacturing method of claim 11, further comprising:
determining, prior to the processing the second measurement data, the random error range of the seed value, wherein the random error range is limited.

* * * * *